United States Patent
Tsubouchi et al.

(10) Patent No.: US 8,292,813 B2
(45) Date of Patent: Oct. 23, 2012

(54) TRANSMISSION MEDIUM FOR ULTRASONIC DIAGNOSIS

(75) Inventors: Toshiyuki Tsubouchi, Chiba (JP); Shoji Aoyama, Tokyo (JP); Mikio Fukuhara, Kanagawa (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 13/088,968

(22) Filed: Apr. 18, 2011

(65) Prior Publication Data

US 2011/0252889 A1    Oct. 20, 2011

Related U.S. Application Data

(62) Division of application No. 10/491,346, filed as application No. PCT/JP02/10047 on Sep. 27, 2002, now abandoned.

(30) Foreign Application Priority Data

Oct. 2, 2001 (JP) ................................. 2001-306713

(51) Int. Cl.
  *A61B 8/00* (2006.01)

(52) U.S. Cl. ......................................... 600/437; 73/600

(58) Field of Classification Search ................. 600/437; 73/600

See application file for complete search history.

(56) References Cited

U.S. PATENT DOCUMENTS

| | | | |
|---|---|---|---|
| 4,997,586 A * | 3/1991 | Mizui et al. | 252/73 |
| 5,283,384 A * | 2/1994 | Abe et al. | 585/22 |
| 5,579,283 A * | 11/1996 | Owens et al. | 367/83 |
| 6,231,508 B1 * | 5/2001 | Miller et al. | 600/437 |
| 6,296,610 B1 * | 10/2001 | Schneider et al. | 600/445 |
| 6,589,054 B2 * | 7/2003 | Tingley et al. | 433/215 |
| 6,788,967 B2 * | 9/2004 | Ben-Haim et al. | 600/424 |
| 6,866,630 B2 * | 3/2005 | Larson et al. | 600/437 |
| 7,402,715 B2 * | 7/2008 | Yoshida et al. | 585/1 |
| 7,815,575 B2 * | 10/2010 | Lo et al. | 600/459 |
| 8,019,501 B2 * | 9/2011 | Breed | 701/31.9 |
| 2009/0247875 A1 * | 10/2009 | Kuniyasu et al. | 600/459 |

* cited by examiner

*Primary Examiner* — Ellen McAvoy
(74) *Attorney, Agent, or Firm* — Oblon, Spivak, McClelland, Maier & Neustadt, L.L.P.

(57) ABSTRACT

Provided is a method of ultrasound diagnosis, wherein the method includes: coating a surface of a specimen with a transmission medium; and performing the ultrasound diagnosis, wherein the transmission medium has a viscosity of at least 1,000 mPa·s at 25° C. and contains a hydrocarbon compound.

14 Claims, 1 Drawing Sheet

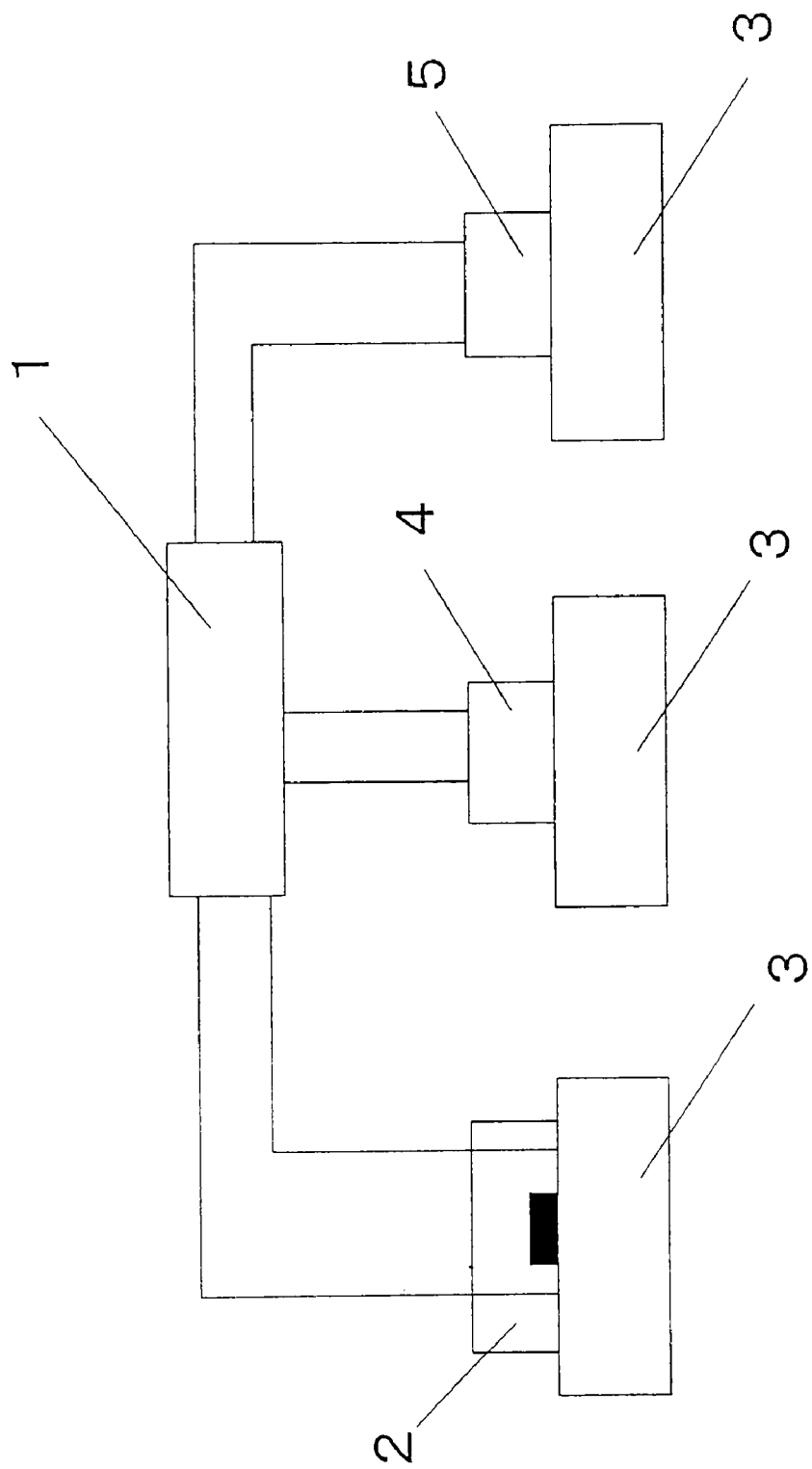

TRANSMISSION MEDIUM FOR ULTRASONIC DIAGNOSIS

CROSS-REFERENCE TO RELATED APPLICATIONS

The present application is a divisional of U.S. patent application Ser. No. 10/491,346, filed on Sep. 27, 2004 now abandoned, which is a 35 U.S.C. §371 National Stage patent application of International patent application PCT/JP2002/010047, filed on Sep. 27, 2002, which claims priority to Japanese patent application JP 2001-306713, filed on Oct. 2, 2001.

FIELD OF THE INVENTION

The present invention relates to a transmission medium for ultrasonic diagnosis, and more particularly to a transmission medium for ultrasonic diagnosis characterized in that said transmission medium contains a hydrocarbon, an ether or an ester and has a specific viscosity.

DISCUSSION OF THE BACKGROUND

In recent years, with regard to ultrasonic flaw detection and ultrasonic diagnosis that are one sort of nondestructive inspection, transverse ultrasonic waves have been used in the majority of instances owing to their favorable detection sensitivity. In the case of carrying out the inspection, a highly viscous transmission medium is used between a test specimen and a probe for the purpose of enhancing the transmission efficiency, wherein polyglycerol and polypropylene glycol are known as a transmission medium.

However, the above-mentioned transmission media are problematical in high hygroscopicity causing rust acceleration in a test specimen after use, decrease in the transmission efficiency during use and the like. Under such circumstances the development of a transmission medium with low hygroscopicity has eagerly been desired.

In addition, the conventional polyglycerol and polypropylene glycol have been insufficient in adhesivity to a solid called thixotropics, thereby taking 2 to 3 minutes in sticking and film stabilization. It being so, from the viewpoint of enhancing inspection efficiency and the like, there has been sought for a transmission medium capable of measuring immediately after the coating thereof, that is, a transmission medium having favorable adhesivity to any solid.

Moreover, the aforesaid conventional transmission media are problematical in that it is incapable of transmitting transverse ultrasonic waves in the measurement in a non-contact state in which a test specimen and a probe are immersed therein. Thus it has been hoped to develop a transmission medium capable of transmitting transverse ultrasonic waves even in a non-contact state.

SUMMARY OF THE INVENTION

It is an object of the present invention to provide a transmission medium for ultrasonic diagnosis which is free from hygroscopicity causing rust generation in a test specimen and worsening the transmission characteristics during use, can impart adhesiveness to a solid within a short period of time, and is particularly excellent in transverse ultrasonic wave transmission.

It is another object of the present invention to provide a transmission medium for ultrasonic diagnosis which is excellent in transverse ultrasonic wave transmission even in a non-contact state in which a test specimen is immersed.

As a result of intensive extensive research and investigation accumulated by the present inventor in order to solve the above-mentioned subject, it has been found that a transmission medium for ultrasonic diagnosis which comprises a hydrocarbon compound, and/or an ether or ester compound each having a cyclic structure and has a viscosity of at least 1000 mPa·s at a working temperature is minimized in hygroscopicity and is endowed with excellent transmission characteristics. Thus the present invention has been accomplished on the basis of the foregoing findings and information.

BRIEF DESCRIPTION OF THE FIGURE

The FIGURE is a schematic illustration showing a method for evaluating the ultrasonic wave transmission characteristics in the present invention.

DETAILED DESCRIPTION OF THE INVENTION

The ultrasonic wave as mentioned in the present invention, which means an elastic wave higher than audible frequency range, is a general idea including any of shear horizontal wave (SH wave), shear vertical wave (SV wave) and longitudinal wave (L wave).

It is indispensable that the transmission medium according to the present invention has a viscosity at a working temperature, that is a measurement temperature being at least 1000 mPa·s, preferably in the range of 1,000 to 300,000 mPa·s, more preferably in the range of 1,000 to 150,000 mPa·s. The viscosity thereat, when being lower than 1000 mPa·s, brings bout incapability of transmitting a transverse ultrasonic wave, whereas the viscosity, when being higher than 300,000 mPa·s, leads to inferior handleability due to unreasonably high viscosity, thereby causing difficulties in usage as a transmission medium as the case may be. The hydrocarbon compound to be used in the present invention is not specifically limited provided that the above-mentioned requirement on the viscosity is satisfied, but is preferably a rigid compound having a cyclic structure and/or a quaternary carbon atom.

Specific examples of the above-mentioned hydrocarbon compounds include dipentene oligomer hydride, polybutene, dicyclopentadiene oligomer hydride, dicyclopentadiene-styrene oligomer hydride, polyphenyl ether, styrene oligomer, styrene oligomer hydride, α-methylstyrene oligomer and α-methylstyrene oligomer hydride. Of these, a saturated alicyclic compound is preferable, of which are particularly preferable 2-methyl-3-methyl-2[(3-methylbicyclo[2,2,1]hept-2-yl)methyl]bicyclo[2,2,1]-heptane and 3-methyl-2-[(3-methylbicyclo[2,2,1]hept-2-yl)methyl]-2-[2,3-dimethylbicyclo-[2,2,1]hept-2-yl]methyl]bicyclo[2,2,1]heptane.

In addition, it is indispensable that the ether or ester in the present invention satisfies the requirement on the viscosity and at the same time, has a cyclic structure. The reason for this is that the compound having a flexible structure free from a cyclic structure is inferior in transverse ultrasonic wave transmission characteristics.

Specific examples of the above-mentioned cyclic structure include saturated rings such as cyclohexane ring, decalin ring, cyclopentane ring, bicyclo[2,2,1]heptane ring, bicyclo[2,2,2]octane ring, bicyclo[3,2,1]octane ring and bicyclo[3,3,0]octane, and aromatic rings such as benzene ring, naphthalene ring, anthracene ring, fluorene ring, indan ring and acenaphthene ring.

In the case where the above-exemplified compound has extremely high viscosity, or is in the form of a resin, it may be mixed with a mixing base material such as a paraffin base hydrocarbon and/or an ester compound. The mixing ratio, which may be arbitrarily selected within the scope that the requirement on the viscosity is satisfied by the mixing, is in the range of usually 1 to 95% by mass, preferably 5 to 80% by mass.

EXAMPLES

In what follows, the present invention will be described in more detail with reference to working examples, which however shall never limit the present invention thereto.

{Method for Evaluating Ultrasonic Wave Transmission Characteristics}

The FIGURE is a schematic illustration showing a method for evaluating the ultrasonic wave transmission characteristics in the present invention.

Opposed type probe for a shear horizontal wave (SH wave) 2, opposed type probe for a shear vertical wave (SV wave) 5, and opposed type probe for a longitudinal wave (L wave) 4 were adhesively fixed onto test specimens 3 made of stainless steel SUS 304 at a constant stress (13 MPa). Subsequently, any of the transmission media in examples and comparative examples was applied as a coating to the interface between the SH probe and the SUS 304, and a measurement was made of the reception sensitivity (V) at room temperature (25° C.) by the use of SH wave and L wave each having a frequency of 5 MHz. A ultrasonic diagnosis instrument 1 (manufactured by Toshiba Tungaloy Co., Ltd. under the trade name "USH-B") was used for the transmission and reception of ultrasonic waves and the analysis of the waveform.

Example 1

In a 2 liter autoclave made of stainless steel were placed 561 g (8 mol) of crotonaldehyde and 352 g (2.67 mol) of dicyclopentadiene to proceed with reaction at 170° C. for 3 hours. After cooling the reaction product, the autoclave was charged with 18 g of Raney nickel catalyst (manufactured by Kawaken Fine Chemicals Co., Ltd. under the trade name "M-300T") to carry out hydrogenation at a hydrogen pressure of 9 kg/cm$^2$ at a reaction temperature of 150° C. for 4 hours. After cooling the reaction product the catalyst was filtered away, and the resultant filtrate was distilled under reduced pressure, so that 565 g of distillate of 105° C./20 mmHg was obtained. Through the analysis by means of mass spectrometric spectrum and nuclear magnetic resonance spectrum, the resultant distillate was identified as 2-hydroxymethylbicyclo[2,2,1]heptane.

Subsequently, 20 g of γ-alumina (manufactured by Nikki Chemical Co., Ltd. under the trade name "N612N") was placed in a flow system atmospheric pressure tubular reactor made of quartz glass measuring 20 mm in outside diameter and 500 mm in length, so that dehydration reaction was put into practice at a reaction temperature of 285° C. at a weight hourly space velocity (WHSV) of 1.1 hr$^{-1}$. As a result, there was obtained a dehydrated reaction product of 2-hydroxymethyl-3-methylbicyclo[2,2,1]heptane which contained both 2-methylene-3-methylbicyclo[2,2,1]heptane and 2,3-dimethylbicyclo[2,2,1]hept-2-ene.

Subsequently, in a 500 milliliter four-necked flask were placed 4.0 g of trifluoroboron diethyl ether complex and 200 g of the olefin compound obtained in the above-mentioned procedure, and the resultant mixture was subjected to oligomerizing reaction at 20° C. for 6 hours under stirring by the use of a mechanical stirrer. The resultant reaction mixture was washed with dilute aqueous solution of sodium hydroxide and saturated common salt water and then, was hydrogenated in a one liter autoclave, while adding therein 6.0 g of a nickel/diatomaceous earth-based hydrogenation catalyst (manufactured by Nikki Chemical Co., Ltd. under the trade name "N-113"). The hydrogenation was carried out under the conditions including a hydrogen pressure of 3 MPa, a reaction temperature of 250° C. and a reaction time of 5 hours. After the completion of the reaction, the catalyst was removed by means of filtration, and the resultant filtrate was distilled under reduced pressure. As a result, there were obtained 145 g of 2-methyl-3-methyl-2[(3-methylbicyclo[2,2,1]hept-2-yl)methyl]bicyclo-[2,2,1]heptane as a 1333 Pa distillate having a boiling point of 160 to 163° C. (hereinafter referred to as "Fluid 1"), and 30 g of 3-methyl-2-[(3-methylbicyclo[2,2,1]hept-2-yl)methyl]-2-[2,3-dimethylbicyclo-[2,2,1]hept-2-yl)methyl]bicyclo[2,2,1]heptane as a 1333 Pa distillate having a boiling point of 240 to 250° C. (hereinafter referred to as "Fluid 2").

An evaluation was made of ultrasonic wave transmission characteristics of a mixture of the Fluid 2 (79% by weight) and the Fluid 1 (21% by weight) as the transmission medium. The results are given in Table 1.

Examples 2 to 12 and Comparative Examples 1 to 7

There were prepared the samples each comprising the substances and having mixing proportion as given in Table 1, and evaluations were made of ultrasonic wave transmission characteristics of each of the mixtures as the transmission medium. The results are given in Table 1.

As a result, the transmission medium for ultrasonic diagnosis according to the present invention has high reception sensitivity for transverse ultrasonic waves and at the same time, has reception sensitivity for longitudinal ultrasonic waves which is comparable to that of conventional glycerol based transmission media.

Comparative Example 8

Evaluations were made of ultrasonic wave transmission characteristics of polyglycerol based transmission medium available on the market immediately after coating and 5 minutes after coating. The results are given in Table 1.

The polyglycerol based transmission medium available on the market revealed marked deterioration in reception sensitivity with the lapse of time.

Example 13

Evaluations were made of ultrasonic wave transmission characteristics of the transmission medium same as in Example 1, 5 minutes after coating.

As a result, no deterioration in reception sensitivity was observed with the lapse of time.

TABLE 1

| Substance (wight %) | Example No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Fluid 1 | 21 | | | 40 | 50 | 50 | 55 | 60 | | | | |
| Fluid 2 | 79 | 100 | 78 | | | | | | | | | |
| Mineral oil*1 | | | 22 | | | | | | | 56 | | |
| Hydrogenated turpentine resin*2 | | | | 60 | 50 | | | | | 44 | 48 | |
| Hydrogenated petroleum resin*3 | | | | | | 50 | 45 | 40 | | | | |
| Hydrogenated dipentene dimer*4 | | | | | | | | | | | 52 | |
| Polybutene*5 | | | | | | | | | | | 100 | |
| Polyphenyl ether*6 | | | | | | | | | | | | 100 |
| Viscosity (mPa·s @25□) | 12000 | 200000 | 8500 | 200000 | 18500 | 65000 | 16000 | 5700 | 8400 | 55000 | 21000 | 1200 |
| Reception sensitivity for SH wave (V) | 0.88 | 1.66 | 0.55 | 0.97 | 0.67 | 0.51 | 0.25 | 0.11 | 0.54 | 0.76 | 0.53 | 0.12 |
| Reception sensitivity for L wave (V) | 0.26 | 0.11 | 0.27 | 0.12 | 0.26 | 0.06 | 0.07 | 0.11 | 0.17 | 0.13 | 0.11 | 0.68 |

| Substance (weight %) | Comparative Example No. | | | | | | | | 8 (5 min after coating) | Example 13 (5 min after coating) |
|---|---|---|---|---|---|---|---|---|---|---|
| | 1 | 2 | 3 | 4 | 5 | 6 | 7 | 8 | | |
| Silicone oil*7 | 100 | | | | | | | | | |
| Silicone oil*8 | | 100 | | | | | | | | |
| Silicone oil*9 | | | 100 | | | | | | | |
| Silicone oil*10 | | | | 100 | | | | | | |
| Fluid 1 | | | | | 50 | | | | | 21 |
| Fluid 2 | | | | | 50 | | | | | 79 |
| Polypropylene glycol*11 | | | | | | 100 | | | | |
| Mineral oil*1 | | | | | | | 100 | | | |
| Polyglycerol | | | | | | | | 100 | 100 | |
| Viscosity (mPa·s @25° C.) | 5000 | 10000 | 30000 | 100000 | 530 | 650 | 220 | 140000 | 140000 | 12000 |
| Reception sensitivity for SH wave (V) | 0.02 | 0.02 | 0.02 | 0.02 | 0.02 | 0.02 | 0.02 | 0.99 | 0.67 | 0.88 |
| Reception sensitivity for L wave (V) | 0.01 | 0.03 | 0.01 | 0.01 | 0.52 | 0.23 | 0.46 | 0.46 | 0.34 | 0.26 |

{Remarks}
*1 paraffin base mineral oil P-500
*2 manufactured by Yasuhara Chemical Co., Ltd. under trade name "Clearon P-85"
*3 manufactured by Idemitsu Petrochemical Co., Ltd. under the trade name "Aimarb P100"
*4 manufactured by Yasuhara Chemical Co., Ltd. under the trade name "YS OilDH"
*5 manufactured by Idemitsu Petrochemical Co., Ltd. under the trade name "Polybutene 100H"
*6 manufactured by Matsumura Oil Research Corporation under the trade name "Polyphenyl ether 5P4E"
*7 manufactured by Toray Silicone Co., Ltd. under the trade name "Silicone Oil SH200-5000cs"
*8 manufactured by Toray Silicone Co., Ltd. under the trade name "Silicone Oil SH200-10000cs"
*9 manufactured by Toray Silicone Co., Ltd. under the trade name "Silicone Oil SH200-30000cs"
*10 manufactured by Toray Silicone Co., Ltd. under the trade name "Silicone Oil SH200-100000cs"
*11 Polypropylene glycol, triol type, manufactured by Wako Pure Chemical Industries Co., Ltd.

INDUSTRIAL APPLICABILITY

The transmission medium for ultrasonic waves according to the present invention is a transmission medium for ultrasonic diagnosis which is free from hygroscopicity causing rust generation in a test specimen and worsening the transmission characteristics during use, can impart adhesiveness to a solid within a short period of time, and is particularly excellent in ultrasonic wave transmission even in a non-contact state in which a test specimen is immersed. The transmission medium according to the present invention, which can be used for both transverse ultrasonic waves and longitudinal ultrasonic waves, is particularly excellent in the transmission of transverse ultrasonic waves, and as a result, is effectively utilizable for ultrasonic flaw detection, ultrasonic measurement and instrumentation and the like.

The invention claimed is:

1. A method of ultrasound diagnosis, wherein the method comprises:
   coating a surface of a specimen with a transmission medium; and
   performing the ultrasound diagnosis,
   wherein the transmission medium has a viscosity of at least 1,000 mPa·s at 25° C. and comprises a hydrocarbon compound, which is 2-methyl-3-methyl-2[(3-methylbicyclo[2,2,1]hept-2-yl)methyl]bicyclo[2,2,1]-heptane;
   3-methyl-2-[(3-methylbicyclo[2,2,1]hept-2-yl)methyl]-2-[2,3-dimethylbicyclo-[2,2,1]hept-2-yl]methyl]bicyclo[2,2,1]heptane; or a mixture of 2-methyl-3-methyl-2[(3-methylbicyclo[2,2,1]hept-2-yl)methyl]bicyclo[2,2,1]-heptane and 3-methyl-2-[(3-methylbicyclo[2,2,1]hept-2-yl)methyl]-2-[2,3-dimethylbicyclo-[2,2,1]hept-2-yl]methyl]bicyclo[2,2,1]heptane.

2. The method according to claim 1, wherein said performing the ultrasound diagnosis comprises:
transmitting an ultrasonic wave through the transmission medium to the specimen; and
analyzing the ultrasonic wave received through the transmission medium from the specimen.

3. The method according to claim 2, wherein the ultrasonic wave is at least one ultrasonic wave selected from the group consisting of a transverse wave, a shear horizontal wave, a shear vertical wave, and a longitudinal wave.

4. The method according to claim 1, wherein the hydrocarbon compound is 2-methyl-3-methyl-2[(3-methylbicyclo[2,2,1]hept-2-yl)methyl]bicyclo[2,2,1]-heptane.

5. The method according to claim 1, wherein the hydrocarbon compound is 3-methyl-2-[(3-methylbicyclo[2,2,1]hept-2-yl)methyl]-2-[2,3-dimethylbicyclo-[2,2,1]hept-2-yl]methyl]bicyclo[2,2,1]heptane.

6. The method according to claim 1, wherein the hydrocarbon compound is a mixture of 2-methyl-3-methyl-2[(3-methylbicyclo[2,2,1]hept-2-yl)methyl]bicyclo[2,2,1]-heptane and 3-methyl-2-[(3-methylbicyclo[2,2,1]hept-2-yl)methyl]-2-[2,3-dimethylbicyclo-[2,2,1]hept-2-yl]methyl]bicyclo[2,2,1]heptane.

7. The method according to claim 1, wherein the transmission medium has a viscosity of 1,000-300,000 mPa·s at 25° C.

8. The method according to claim 1, wherein the transmission medium has a viscosity of 1,000-150,000 mPa·s at 25° C.

9. The method according to claim 1, wherein the transmission medium further comprises an ether compound comprising a cyclic structure.

10. The method according to claim 9, wherein the ether compound comprises a cyclic structure comprising a saturated ring selected from the group consisting of a cyclohexane ring, a decalin ring, a cyclopentane ring, a bicyclo[2,2,1]heptane ring, a bicyclo[2,2,2]octane ring, a bicyclo[3,2,1]octane ring, and a bicyclo[3,3,0]octane ring.

11. The method according to claim 9, wherein the ether compound comprises a cyclic structure comprising an aromatic ring selected from the group consisting of a benzene ring, a naphthalene ring, an anthracene ring, a fluorene ring, an indan ring, and an acenaphthene ring.

12. The method according to claim 1, wherein the transmission medium further comprises an ester compound comprising a cyclic structure.

13. The method according to claim 12, wherein the ester compound comprises a cyclic structure comprising a saturated ring selected from the group consisting of a cyclohexane ring, a decalin ring, a cyclopentane ring, a bicyclo[2,2,1]heptane ring, a bicyclo[2,2,2]octane ring, a bicyclo[3,2,1]octane ring, and a bicyclo[3,3,0]octane ring.

14. The method according to claim 12, wherein the ester compound comprises a cyclic structure comprising an aromatic ring selected from the group consisting of a benzene ring, a naphthalene ring, an anthracene ring, a fluorene ring, an indan ring, and an acenaphthene ring.

* * * * *